United States Patent
Chen et al.

(10) Patent No.: US 9,951,358 B2
(45) Date of Patent: Apr. 24, 2018

(54) METHODS OF USING CAPSAICIN SYNTHASE FOR THE MICROBIAL PRODUCTION OF CAPSAICINOIDS

(71) Applicant: Conagen Inc., Bedford, MA (US)

(72) Inventors: Hui Chen, Bedford, MA (US); Hongxue Wang, Jiangsu (CN); Oliver Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 15/111,901

(22) PCT Filed: Jan. 16, 2015

(86) PCT No.: PCT/US2015/011729
§ 371 (c)(1),
(2) Date: Jul. 15, 2016

(87) PCT Pub. No.: WO2015/109168
PCT Pub. Date: Jul. 23, 2015

(65) Prior Publication Data
US 2016/0340701 A1    Nov. 24, 2016

Related U.S. Application Data

(60) Provisional application No. 61/928,803, filed on Jan. 17, 2014.

(51) Int. Cl.
*C12P 13/02* (2006.01)
*C12N 9/20* (2006.01)
(Continued)

(52) U.S. Cl.
CPC ............ *C12P 13/02* (2013.01); *A61K 31/165* (2013.01); *C12N 9/1029* (2013.01);
(Continued)

(58) Field of Classification Search
None
See application file for complete search history.

(56) References Cited

U.S. PATENT DOCUMENTS 6,022,718 A * 2/2000 Iwai ............... C12P 7/6436
435/129
2003/0157670 A1* 8/2003 Nakanishi ............ C12P 13/02
435/129
(Continued)

FOREIGN PATENT DOCUMENTS

CN     103725652 A     4/2014
IN     402 009 A1     10/2009
(Continued)

OTHER PUBLICATIONS

Prasad et al., Characterization of capsaicin synthase and identification of its gene (csy1) for pungency factor capsaicin in pepper (*Capsicum* sp.). Proc Natl Acad Sci U S A. Sep. 5, 2006;103(36):13315-20. Epub Aug. 28, 2006. Erratum in: Proc Natl Acad Sci U S A. Apr. 17, 2007;104(16):6876. Retraction in: Prasad et al., Proc Natl Acad Sci U S A. Dec. 23, 2008;105(51):20558.

(Continued)

*Primary Examiner* — Richard C Ekstrom
(74) *Attorney, Agent, or Firm* — Wolf, Greenfield & Sacks, P.C.; Byron V. Olsen

(57) ABSTRACT

A biosynthetic method of making a capsaicinoid including expressing a first gene product of CS/AT3/Pun1 in a cellular system, growing the cellular system in a medium, and collecting the capsaicinoid. The biosynthetic method further includes expressing a second gene product of ACS1 and expressing a third gene product of pAMT in the cellular system.

10 Claims, 12 Drawing Sheets

(51) Int. Cl.
*A61K 31/165* (2006.01)
*C12N 9/10* (2006.01)
*C12N 9/00* (2006.01)
*C12N 15/52* (2006.01)

(52) U.S. Cl.
CPC ............ *C12N 9/1096* (2013.01); *C12N 9/20* (2013.01); *C12N 9/93* (2013.01); *C12N 15/52* (2013.01); *C12Y 602/01001* (2013.01)

(56) References Cited

U.S. PATENT DOCUMENTS

2004/0033530 A1   2/2004   Awrey et al.
2011/0166371 A1   7/2011   Kisaka et al.

FOREIGN PATENT DOCUMENTS

WO   WO 2013/006953 A1   1/2013
WO   WO 2015/109168 A1   7/2015

OTHER PUBLICATIONS

Ruan et al., Capsicum annuum cultivar Yidu-Red inbred 201 acyltransferase (Pun1) mRNA, complete cds. GenBank Accession No. GU300812.1. Dated Jan. 17, 2010. [https://www.ncbi.nlm.nih.gov/nuccore/283766072].

Stewart et al., The Pun1 gene for pungency in pepper encodes a putative acyltransferase. Plant J. Jun. 2005;42(5):675-88.

PCT/US2015/011729, dated Apr. 9, 2015, International Search Report and Written Opinion.

PCT/US2015/011729, dated Jul. 28, 2016, International Preliminary Report on Patentability.

Del Rosario Abraham-Juárez M et al., Virus-induced silencing of Comt, pAmt and Kas genes results in a reduction of capsaicinoid accumulation in chili pepper fruits. Planta. Feb. 2008;227(3):681-95. Epub Nov. 13, 2007.

Prasad et al., Influence of 8-methyl-nonenoic acid on capsaicin biosynthesis in in-vivo and in-vitro cell cultures of Capsicum spp. J Agric Food Chem. Mar. 8, 2006;54(5):1854-9.

Prasad et al., Valine pathway is more crucial than phenyl propanoid pathway in regulating capsaicin biosynthesis in Capsicum frutescens mill. J Agric Food Chem. Sep. 6, 2006;54(18):6660-6.

Ramachandra et al., Biotransformation of isoeugenol to vanilla flavour metabolites and capsaicin in suspended and immobilized cell cultures of Capsicum frutescens: study of the influence of β-cyclodextrin and fungal elicitor. Process Biochem. Nov. 1999;35(3-4):341-348.

Stewart et al., Genetic control of pungency in C. chinense via the Pun1 locus. J Exp Bot. 2007;58(5):979-91. Epub Mar. 5, 2007.

Sudhakar Johnson et al., Biotransformation of ferulic acid and vanillylamine to capsaicin and vanillin in immobilized cell cultures of Capsicum frutescens. Plant Cell Tiss Organ Cult. Feb. 1996;44(2):117-121.

\* cited by examiner

SEQUENCE LISTING

```
<160> NUMBER OF SEQ ID NOS: 7

<210> SEQ ID NO 1
<211> LENGTH: 1323
<212> TYPE: DNA
<213> ORGANISM: Ghost Chili Pepper

<400> SEQUENCE: 1
atggcttttg cattaccatc atcacttgtt tcagtttgtg acaaatcttt tatcaaacct      60
tcctctctca cccctctaa acttagattt cacaagctat ctttcatcga tcaatcttta     120
agtaatatgt atatccttg tgcattttt taccctaaag tacaacaaag actagaagac      180
tccaaaaatt ctgatgagct ttcccatata gcccacttgc tacaaacatc tctatcacaa   240
actctagtct cttactatcc ttatgcagga aagttgaagg acaatgctac tgttgactgt    300
aacgatatgg gagctgagtt cttgagtgtt cgaataaaat gttccatgtc tgaaattctt    360
gatcatcctc atgcatctct tgcagagagc atagttttgc ccaaggattt gccttgggcg   420
aataattgtg aaggtggtaa tttgcttgta gttcaagtaa gtaagtttga ttgtggggga   480
atagccatca gtgtatgctt ttcgcacaag attggtgatg gttgctctct gcttaatttc    540
cttaatgatt ggtctagcgt tactcgtgat catacgacaa cagctttagt tccatctcct    600
agatttgtag gagattctgt cttctctaca aaaaaatatg ttctcttat tacgccacaa    660 attttgtccg atctcaacga gtgcgtacag aaaagactca tttttcctac agataagtta    720
gatgcacttc gagctaaggt ggcagaagaa tcaggagtaa aaaatccaac aagggcagaa    780
gttgttagcg ctcttctttt caaatgtgca acaaaggcat catcatcaat gctaccatca    840
aagttggttc acttcttaaa catacgtact atgatcaaac ctcgtctacc acgaaatgcc    900
attggaaatc tctcgtctat tttctccata gaagcaacta acatgcagga catggagttg    960
ccaacgttgg ttcgtaattt aaggaaggaa gttgaggtgg catacaagaa agaccaagtc   1020
gaacaaaatg aactgatcct agaagtagta gaatcaatga gagaagggaa actgccatt    1080 gaaaatatgg atggctatga gaatgtgtat acttgcagca atctttgcaa atatccgtac   1140
tacactgtag attttggatg gggaagacct gaaagagtgt gtctaggaaa tggtccctcc  1200
aagaatgcct tcttcttgaa agattacaaa gctgggcaag gcgtggaggc gcgggtgatg  1260
ttgcacaagc aacaaatgtc tgaatttgaa cgcaatgagg aactccttga gttcattgcc   1320
taa                                                                 1323

<210> SEQ ID NO 2
<211> LENGTH: 24
<212> TYPE: DNA
```

```
<213> ORGANISM: Artificial Sequence
<220> FEATURE:
<223> OTHER INFORMATION: One of the primers for the initial cloning of
      CS/AT3/Pun1 gene was into the pENTR/D_TOPO vector

<400> SEQUENCE: 2
caccatggct tttgcattac catc                                              24

<210> SEQ ID NO 3
<211> LENGTH: 21
<212> TYPE: DNA
<213> ORGANISM: Artificial Sequence
<220> FEATURE:
<223> OTHER INFORMATION: One of the primers for the initial cloning of
      CS/AT3/Pun1 gene into the pENTR/D_TOPO vector

<400> SEQUENCE: 3
ttaggcaatg aactcaagga g                                                 21

<210> SEQ ID NO 4
<211> LENGTH: 35
<212> TYPE: DNA
<213> ORGANISM: Artificial Sequence
<220> FEATURE:
<223> OTHER INFORMATION: Primers for cloning CS/Pun1/AT3 gene into
      pETite N-His SUMO Kan expression vector.

<400> SEQUENCE: 4
cgcgaacaga ttggaggtgc ttttgcatta ccatc                                  35

<210> SEQ ID NO 5
<211> LENGTH: 39
<212> TYPE: DNA
<213> ORGANISM: Artificial Sequence
<220> FEATURE:
<223> OTHER INFORMATION: Primer for cloning CS/Pun1/AT3 gene into
      pETite N-His SUMO Kan expression vector.

<400> SEQUENCE: 5
gtggcggccg ctctattatt aggcaatgaa ctcaaggag                              39

<210> SEQ ID NO 6
<211> LENGTH: 27
<212> TYPE: DNA
<213> ORGANISM: Artificial Sequence
<220> FEATURE:
<223> OTHER INFORMATION: One of the primers for the cloning of ACS1 into
      pCDFDuet-1 vector.

<400> SEQUENCE: 6
gaagatctat ggcaacagat aaattta                                           27

<210> SEQ ID NO 7
<211> LENGTH: 28
<212> TYPE: DNA
<213> ORGANISM: Artificial Sequence
<220> FEATURE:
<223> OTHER INFORMATION: One of the primers for the cloning of ACS1 into
      pCDFDuet-1 vector.

<400> SEQUENCE: 7
ccgctcgagt cacttggtac ccttgtac                                          28
```

METHODS OF USING CAPSAICIN SYNTHASE FOR THE MICROBIAL PRODUCTION OF CAPSAICINOIDS

CROSS-REFERENCE TO RELATED APPLICATIONS

This application is a national stage filing under 35 U.S.C. § of International PCT Application, PCT/US2015/011729, filed Jan. 16, 2015, entitled Methods of Using Capsaicin Synthase for the Microbial Production of Capsaicinoids, which claims priority to U.S. Provisional Patent application No. 61/928,803 filed on Jan. 17, 2014, the contents of each of which are incorporated by reference herein in their entirety.

BACKGROUND OF THE DISCLOSURE

Field of Disclosure

This disclosure relates generally to a method for the biosynthetic production of capsaicin and related capsaicinoids, particularly utilizing acyl-CoA synthetase (ACS), aminotransferase (pAMT) and capsaicin synthase (CS).

Background Art

The chili pepper is the fruit from plants of the genus *Capsicum*, members of the nightshade family, Solanaceae. Chili pepper has been widely used as a food additive in spicy and hot cuisines, due to its pungent nature. Capsacinoids are the substances responsible for the pungent sensation of the chili pepper and as mentioned previously, their production is restricted to the genus *Capsicum*. Capsaicin (CP, 8-methyl-N-vanillyl-trans-6-nonenamide) and dihydrocapsaicin (DHCP, 8-methyl-N-vanillylnonanamide) are the two major capsaicinoids responsible for roughly up to 90% of the pungency in chili pepper (Garcés-Claver, et al., 2007).

In addition to being used mainly as food additives for hot sensation and spicy flavoring, capsaicinoids have many pharmaceutical and medical uses. They have been found to exert a series of physiological and pharmacological effects, including analgesia, anti-cancer, anti-inflammatory, anti-oxidative and anti-obesity activities and are used as the main components ointments, patches, oils and creams designed to relieve the pain caused by several diseases such as vasomotor rhinitis, osteoarthritis and rheumatoid arthritis (Aza-González, et al., 2011). Capsaicinoids are also currently used as the main active ingredient in self-protective aerosol sprays (i.e., pepper sprays) on the market (Reilly, et al., 2001). Recently capsaicinoids were reported to lower plasma cholesterol and improve endothelial function in hamsters (Liang, et al., 2013).

Capsaicin is believed to be synthesized by CS, an acyltransferase that transfers the 8-methylnonenoyl moiety from 8-methylnonenoyl-CoA to vanillylamine to form an amide conjugate (FIG. 1). Vanillylamine is formed from the phenylpropanoid pathway wherein the branched-chain fatty acid is derived from a branched-chain amino acid, e.g., valine (Curry, et al., 1999; Mazourek, et al., et al., 2009). The aminotransferase (pAMT) catalyzes the formation of vanillyamine from vanillin. Applicants have cloned pAMT derived from ghost chili pepper. The other substrate, 8-methylnonenoyl-CoA, is derived from 8-methyl-trans-6-nonenoic acid through the activity of an acyl-CoA synthetase (ACS).

In this disclosure, applicants have utilized the gene product of CS to produce capsaicinoids by microbial biosynthesis. Applicants are the first to achieve microbial production of capsaicinoids, particularly capsaicin. Moreover, this invention addresses a long-felt but unmet need in the industry to produce capsaicin by microbial biosynthesis.

BRIEF SUMMARY OF DISCLOSURE

This present disclosure is a method of bioconversion making a capsaicinoid comprising expressing a first gene product of CS/AT3/Pun1 in a mixture, providing a first substrate to the mixture, and collecting the capsaicinoid.

Another present disclosure is a method of bioconversion making a capsaicinoid including expressing a first gene product of CS/AT3/Pun1 in a cellular system, growing the cellular system in a medium, and collecting the capsaicinoid.

Another present disclosure is a method of bioconversion making a plurality of capsaicinoid comprising expressing a gene product of CS/AT3/Pun1 in a cellular system, providing 8-methyl-6-nonenoyl-CoA, providing vanillylamine, growing the cellular system in a medium, and collecting the plurality of capsaicinoid, wherein the plurality capsaicinoid is more than about 90% capsaicin and less than about 5% of dihydrocapsaicin by numerical ratio or molar ratio.

Another present disclosure is a method of bioconversion making a plurality of capsaicinoid comprising expressing a gene product of CS/AT3/Pun1 in a cellular system, providing 8-methyl-nonanoyl-CoA, providing vanillylamine, growing the cellular system in a medium, and collecting the plurality of capsaicinoid, wherein the plurality of capsaicinoid is more than about 90% dihydrocapsaicin and less than about 5% capsaicin by ratio.

Another disclosure is a biosynthetic method of making a capsaicinoid comprising expressing a gene product of CS/AT3/Pun1 in a cellular system, providing fatty acid-CoA (an activated form of fatty acid), providing vanillylamine, growing the cellular system in a medium, and collecting the capsaicinoid.

BRIEF DESCRIPTIONS OF THE DRAWINGS

For a better, understanding of the present disclosure, reference may be made to the accompanying drawings in which:

FIG. 1 shows the capsaicin biosynthetic pathway. Adapted from Stewart et al. (2007).

FIG. 2 shows the HPLC profiles of products extracted from *E. coli* BL21 cells overexpressing the genes ACS1 and CS/AT3/Pun1 upon the feeding of substrates. 1: Capsaicin (CP) and 2: dihydrocapsaicin (DHCP). (A) A mixture of CP and DHCP standards from Sigma; (B) the control without the feeding substrates; (C) feeding with vanillylamine (VN) and 8-methyl-6-nonenoic acid (6E); (D) feeding with VN and 8-methyl nonanoic acid (8M); (E) feeding with VN, 6E and 8M.

FIG. 3 shows GC/MS profile of capsaicin and dihydrocapsaicin standards obtained from Sigma (Cat. No. 360376 Sigma, a mixture of CP and DHCP).

FIG. 4 shows GC/MS profiles of products from the feeding of different substrates (e.g., VN, 6E and 8M) to the BL21 cultures overexpressing ACS1 and CS/AT3/Pun1. The GC/MS analysis was performed with a Shimadzu GC-2010 system coupled with a GCMS-QP2010S detector. Column Rtx-5MS (thickness 0.25 u; length 30 m; diameter 0.25 mm) was used for separation. Injection temperature: 265° C.; injection mode: split; oven temperature: 140° C. The temperature gradient: 0-1 min, 140° C.; 1-11.25 min, 140° C. to 263° C., rate 12; 11.25-21.25 min, 263° C.

FIG. 5 shows MS of the products from the feeding of substrates (6E and 8M) compared with capsaicin (CP) and dihydrocapsaicin (DHCP) control profiles.

FIG. 6 shows SDS-PAGE analysis of His-SUMO-Pun1 expression in BL21 (DE3) cells. 0, 20: total protein at the times after IPTG induction; C, soluble crude protein extract; E1 to E3, fractions eluted from Ni-NTA column. The molecular weight of Pun1 is ca. 49 Kd and that of His-SUMO tag is ca. 12 Kd.

Figure 12:
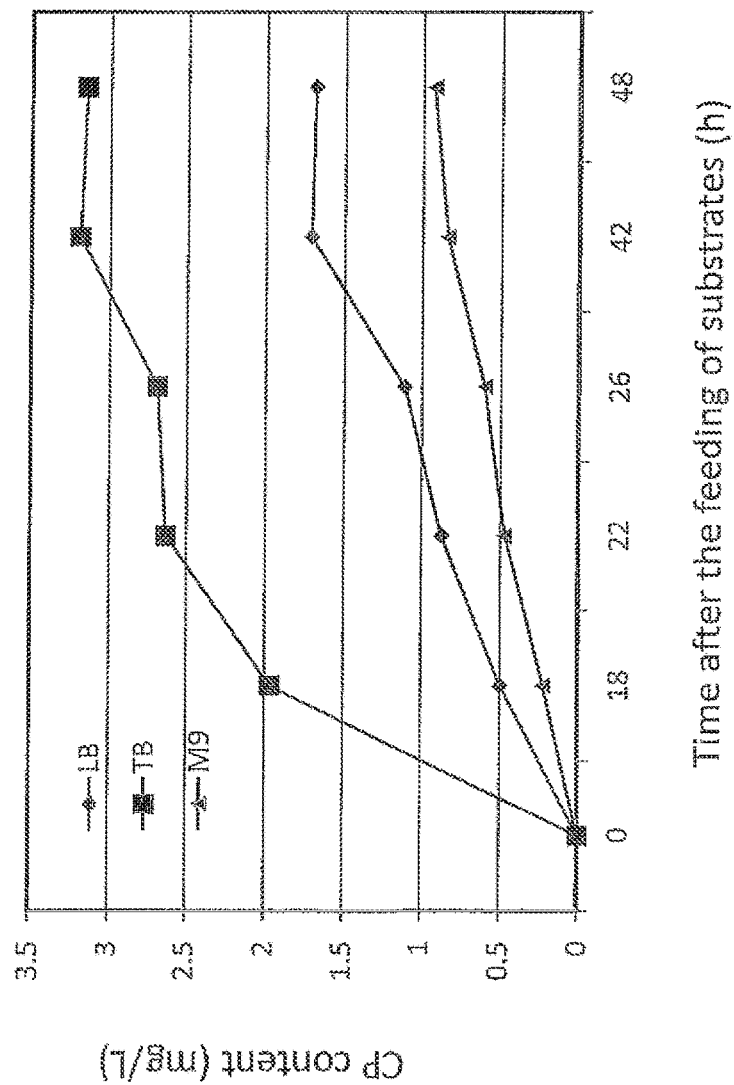

FIG. 12 shows effect of culture media on the production of capsaicin (CP) from the feeding of 50 mg/L of vanillyamine (VN) and 50 mg/L of 8-methyl-6-nonenoic acid (6E) in the BL21(DE3) cultures co-overexpressing pCDFDuet-ACS1 and pETite N-His SUMO-ghost Pun1. LB, Luria Broth; TB, Terrific Broth; M9, M9 Minimal Medium. The experiments were performed in triplicate and the averages were used to draw the graphs.

While the disclosure is susceptible to various modifications and alternative forms, specific embodiments thereof are shown by way of example in the drawing and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure as defined by the appended claims.

DETAILED DESCRIPTION OF THE DISCLOSURE

Definitions
Cellular System

Cellular system is any cells that provide for the expression of ectopic proteins. It includes bacteria, yeast, plant cells and animal cells. It includes prokaryotic and eukaryotic cells. It also includes in vitro expression of proteins utilizing cellular components, such as ribosomes.
Growing the Cellular System Growing includes providing medium that would allow cells to multiply and divide. It also includes providing resources so that cells or cellular components can translate and make recombinant proteins.
Protein Expression Protein production can occur after gene expression. It consists of the stages after DNA has been transcribed to messenger RNA (mRNA). The mRNA is then translated into polypeptide chains, which are ultimately folded into proteins. DNA is present in the cells through transfection—a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. Transduction is often used to describe virus-mediated DNA transfer. Transformation, transduction, and viral infection are included under the definition of transfection for this application. In addition, protein expression includes in vitro translation, wherein proteins are expressed utilizing cellular organelles that are outside the cells.
Bioconversion The term bioconversion, also known as biotransformation refers to the use of live organisms often microorganisms (e.g., bacteria and yeast) to carry out a chemical reaction that is more costly or not feasible nonbiologically. These organisms convert a substance to a chemically modified form.
Mixture A mixture refers to the physical combination of two or more substances on which the identities are retained and are mixed in the form of solutions, suspensions, and colloids.
Gene Product A gene product is the biochemical material, either RNA or protein, resulting from expression of a gene.

A disclosure of the current invention is a method of bioconversion making a capsaicinoid comprising expressing a first gene product of CS/AT3/Pun1 in a mixture, providing a first substrate to the mixture, and collecting the capsaicinoid. The first gene product of CS/AT3/Pun1 is based on DNA sequence SEQ ID No. 1. In a further disclosure, the first gene product of CS/AT3/Pun1 is based on DNA sequence with at least about 95% identity to SEQ ID No. 1. In another embodiment, the first gene product of CS/AT3/Pun1 is derived from ghost chili pepper. Moreover, the first substrate is an activated fatty acid selected from the group consisting of 8-methyl-6-nonenoyl-CoA, 8-methyl nonanoyl-CoA, octanoyl-CoA, decanoyl-CoA, and a combination thereof.

Another disclosure includes providing the first substrate to the mixture further comprises by expressing a second gene product of ACS, particularly ACS1 in a mixture and providing a second substrate. In an embodiment, the second gene product of ACS1 is derived from ghost chili pepper. The second substrate is a fatty acid selected from the group consisting of 8-methyl-6-nonenoic acid, 8-methyl nonanoic acid, octanoic acid, decanoic acid, and a combination thereof. Further, in another disclosure, expressing any of the genes occurs by in vitro translation. In another disclosure, expressing any of the genes further occurs expressing the gene in a cellular system. The cellular system is based on a microorganism selected from the group consisting of bacteria, yeast and a combination thereof. The expression product from any of the genes is purified as a recombinant protein. In a further disclosure, a third substrate vanillyamine is provided.

Another disclosure comprises expressing a third gene product of pAMT in a mixture and providing a fourth substrate vanillin. In an embodiment, the third gene product of pAMT is derived from ghost chili pepper. In a disclosure, any of the genes is expressed by in vitro translation. In another disclosure, any of the genes is expressed in a cellular system. The cellular system is based on a microorganism selected from the group consisting of bacteria, yeast and a combination thereof. The expression product from any of the genes can be purified as a recombinant protein.

Another disclosure is comprises expressing a first gene product of CS/AT3/Pun1 in a cellular system, growing the cellular system in a medium; and collecting the capsaicinoid. In one disclosure, the capsaicinoid is a capsaicin. Another embodiment further comprises providing 8-methyl-6-nonenoyl-CoA and providing vanillylamine. The provision of 8-methyl-6-nonenoyl-CoA includes expressing a second gene product of ACS1 in the cellular system and providing the substrate 8-methyl-6-nonenoic acid. The provision of vanillylamine comprises expressing a third gene product of pAMT in the cellular system and providing the substrate vanillin. In another disclosure, the capsaicinoid is a capsaicin. Alternatively or in addition, the capsaicinoid is a dihydrocapsaicin. In terms of producing dihydrocapsaicin, the disclosure further comprises providing 8-methyl-nonanoyl-CoA and providing vanillylamine. In regards to providing 8-methyl-nonanoyl-CoA, it includes expressing a second gene product of ACS, particularly ACS1, in the cellular system and providing 8-methyl nonanoic acid. The disclosure further comprises expressing a third gene product of pAMT in the cellular system and providing the substrate vanillin. The first gene product is expressed from CS/AT3/Pun1 cloned from ghost chili pepper. In an embodiment, the gene product is expressed from CS/AT3/Pun1 that shares a sequence identity of at least about 95% with CS/AT3/Pun1 cloned from ghost chili pepper. The cellular system is selected from the group consisting of bacteria, yeast, and a combination thereof.

Another disclosure is a method of bioconversion making a capsaicinoid comprising expressing a gene product of CS/AT3/Pun1 in a cellular system, providing fatty acid-CoA, providing vanillylamine, growing the cellular system in a medium, and collecting the capsaicinoid. In one disclosure, the fatty acid-CoA is 8-methyl-6-nonenoyl-CoA, and the capsaicinoid is more than about 90% capsaicin by numeric ratio. In another disclosure, the fatty acid-CoA is 8-methyl-nonanoyl-CoA, and the capsaicinoid is more than about 90% dihydrocapsaicin by numeric ratio. In another disclosure, the fatty acid-CoA provided is octanoyl-CoA and the capsaicinoid product is N-vanillyloctamide, more specifically more than about 90% N-vanillyloctamide. In another disclosure, the fatty acid-CoA is decanoyl-CoA and the capsaicinoid product is N-vanillyldecanamide, more specifically more than about 90% N-vanillyldecanamide.

As for the cellular system used in various embodiments, it is selected from the group consisting of bacteria, yeast, and a combination thereof. Any cellular system that would allow the biosynthetic production is provided.

It has been known for a long time that the pungency of pepper is controlled by Pun1 locus and the corresponding gene has recently been identified as AT3, which encodes a putative acyltransferase (Stewart et al., 2005). AT3 is a member of the BAHD acyltransferase superfamily and has been suggested as a putative CS/AT3/Pun1 (Kim et al., 2009). However, the biochemical activity of the gene product of CS/AT3/Pun1 has not been reported thus far. This lack of evidence of biochemical activity is mainly due to the fact that the acyl-CoA substrates for the gene product of CS/AT3/Pun1 are not commercially available and the recombinant expression of CS/AT3/Pun1 has been difficult due to extreme insolubility of the protein (Stewart et al., 2005). It has also been speculated that CS may belong to an acyltransferase family other than the BAHD family (Stewart et al., 2005). Applicants are the first to show that the gene product of CS/AT3/Pun1 possesses CS function in a bioconversion reaction. Applicants have addressed this long-felt but unmet need of making capsaicinoids, particularly capsaicin, in a bioconversion method.

Further, due to the wide use of capsaicinoids in food, medicine and defense (e.g., pepper spray), there has been an increased demand for capsaicinoids. Thus far, hot peppers are the only natural source for capsaicinoids. However, the content of capsaicinoids in hot peppers is generally low and is affected by environmental and growth conditions. For example, a range of 0.22 to 20 mg of total capsaicinoids/g of pepper (dry weight) has been reported (Thomas et al., 1998). The deficiency in the supply of natural capsaicinoids contributes to the extremely high prices for natural capsaicinoids, e.g., US$2,000-3,000/kg (http://www.alibaba.com/product-gs/810894171/Natural_Capsaicin_Capsaicine_Powder_97_16.html?s=p). Having another source for capsaicinoids that can meet the demand has been a long, unmet need in the industry.

Genetically engineered microbes have become an increasingly important platform for the production of drugs, chemicals, and biofuels from renewable resources (Du et al., 2011). These biotechnological products, when used in food, can be labeled as 'natural' in the food industry according to current regulations (Hausler and Winch, 1997). The prerequisite for the development of a microbial production platform is the cloning and characterization of the corresponding genes in the bioconversion pathway. Due to the importance of capsaicinoids, there has been a long interest in the cloning of the gene encoding capsaicin synthase. For example, over 100 years ago, Webber reported that PUN1 locus as a controller of the pungency of pepper (Webber, 1911). The corresponding gene was cloned, which encode the gene product for AT3, an acyltransferases in the BAHD superfamily (Stewart et al., 2005). However, until recently shown by the applicants, no biochemical activity has been ascribed to this putative acyltransferase and the claim that the gene product for CS/AT3/Pun1 is a putative capsaicin synthase was questionable. Moreover, because of the lack of acyl-CoA substrates for the gene product of CS/AT3/Pun1, the activity from the gene product of CS/AT3/Pun1 could never be effectively captured to make capsaicin and other capsaicinoids in a bioconverting mechanism. Later, in another study, using an enzyme-to-gene approach, Prasad et al. (2006) reported the identification of csy1 as the elusive capsaicin synthase gene. However, two years later, this work was retracted (Prasad et al., 2008) and the CS gene remains unidentified and unconfirmed. Accordingly, not only is the biochemical identity and confirmation of the real capsaicin synthase has been a long time goal in the industry, the exploitation of the CS gene in a bioconverting mechanism to make capsaicin and other capsaicinoids has been long desired.

Following applicants' identification of the activity of the gene product for ACS1, applicants were able to make acyl-CoA substrates, and thus, they were able to demonstrate that CS/PUN1/AT3 has CS activity both in vitro and in vivo. This represents the first example of heterologous biosynthesis of capsaicinoids, which paves the way for the development and optimization of microbial fermentation process for the production of "natural" capsaicinoids. Also, in developing this method, applicants have shown that through the feeding of different fatty acid substrates, they were also able to make different species of capsaicinoids that may not occur in nature.

EXAMPLE 1

CS/Pun1/AT3 Gene Product Has CS Activity In Vivo.

Figure 1:
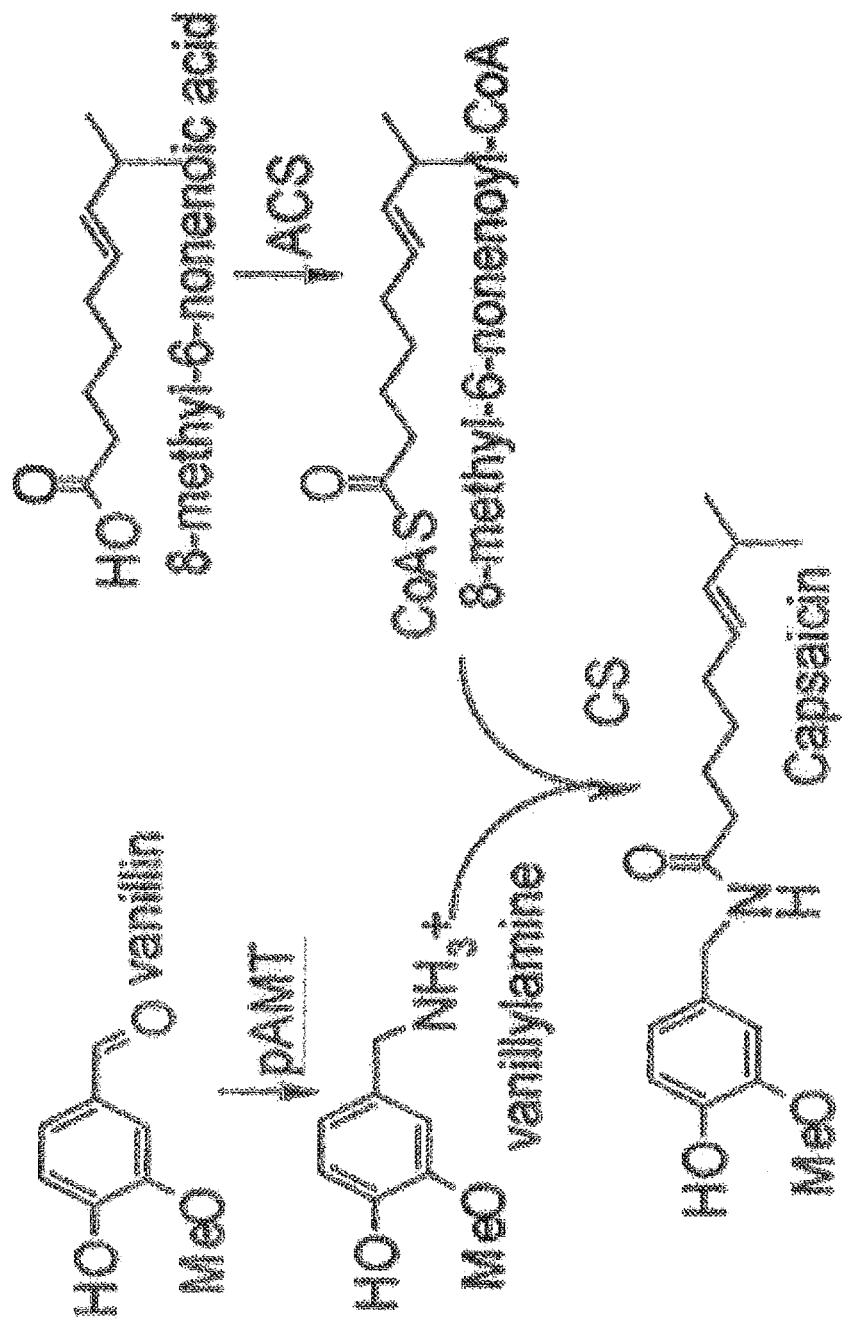
Figure 2:
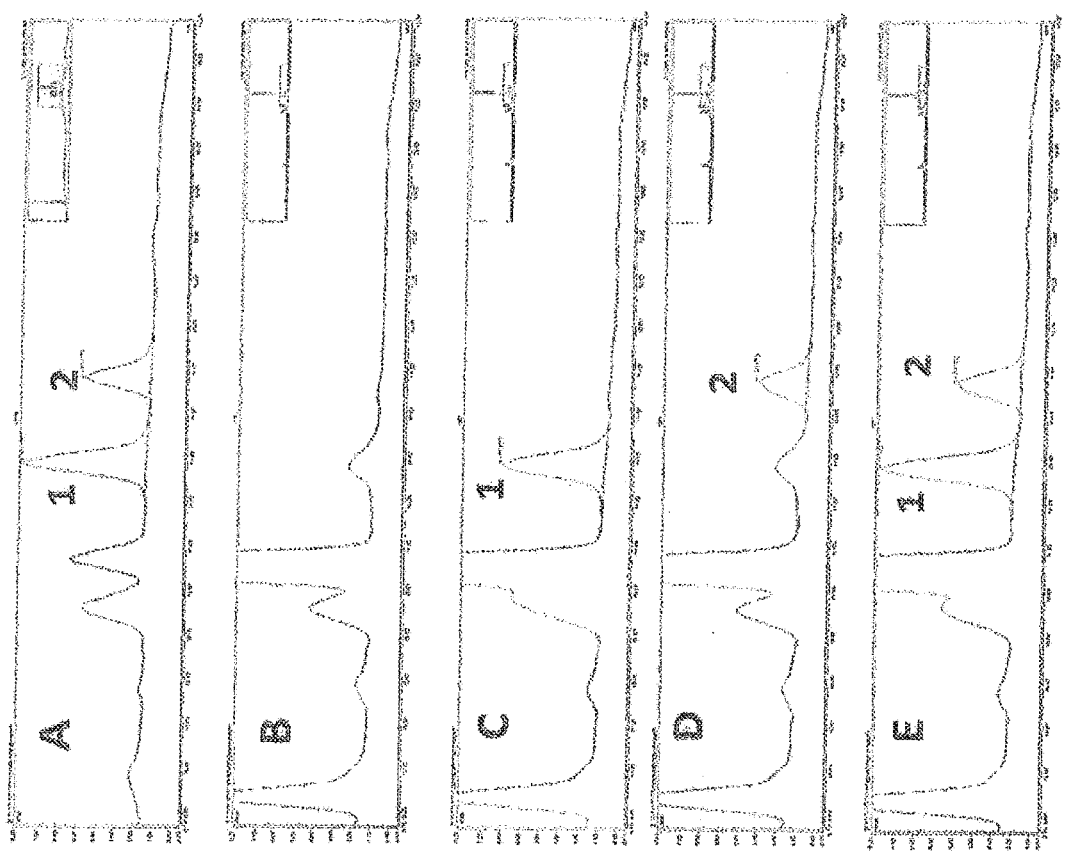

Following applicants' recent discovery of ACS activity from pepper (Chen H, Wang H, and Yu O, U.S. 61/898,944), the gene products of ACS1 and CS/AT3/Pun1 were co-overexpressed in *E. coli* BL21(DE3) cells. Applicants discovered that the gene product of ACS1 has the ability to activate fatty acids by the addition of CoA, making a form of high energy fatty acids. After the induction of protein expression by IPTG and the feeding of vanillyamine (VN) and 8-methyl-6-nonenoic acid (6E)/8-methyl nonanoic acid (8M), putative CP/DHCP was produced (FIG. 2). In nature (i.e., as derived from hot peppers), capsaicin and dihydrocapsaicin are made together, whereas in a biosynthetic reaction, applicants has discovered that they can control the production of capsaicin, dihydrocapsaicin and other capsaicinoids by feeding specific activated fatty acids (e.g., 6E-CoA, 8M-CoA, octanoyl-CoA, and decanoyl-CoA).

Cloning of CS/Pun1/AT3.

The applicants are the first to show biochemically CS activity from gene product of the CS/AT3/Pun1 gene and bioconversion of substrates in a cellular system. Particularly, the applicants showed the ability to catalyze the conversion of activated fatty acid to capsaicinoids. The initial cloning of CS/AT3/Pun1 gene was into the pENTR/D_TOPO vector. The cloning of CS requires the following primers. The primers 309-pentr-F: CACCATGGCTTTTGCATTAC-CATC and 309-pentr-R: TTAGGCAATGAACT-CAAGGAG were used to amplify CS/AT3/Pun1 gene from the cDNA of the green fruits of ghost chili pepper and the resulting PCR product was cloned into pENTR/D_TOPO vector and then swapped into pDEST17 vector by LR reaction (Invitrogen). The gene product for CS/AT3/Pun1 was then expressed in a bacterial system, such as BL21 (DE3), and then CP and DHCP were detected upon providing the necessary substrates. HPLC was performed with Dionex-UltiMate® 3000 LC Systems (Thermo Scientific) using an Acclaim® 120 C18 reversed-phase column (Thermo Scientific; 3µ, 120 Å, 150×3 mm). The mobile phase consisted of solvent A (0.1% trifluoroacetic acid) and solvent B (acetonitrile). The gradient elution procedure was as follows: 0 to 5 min, 5% of B; 5 to 9 min, a linear gradient from 5 to 80% of B; 9 to 11 min, 80% of B; 11 to 12 min, 5% of B. The flow rate was 0.6 ml/min. The diode array detector collected data in the 200- to 400-nm range. For detection and quantification of substrate and products, peak areas were measured at 280 nm.

CP/DHCP Identity Confirmation.

Figure 3:
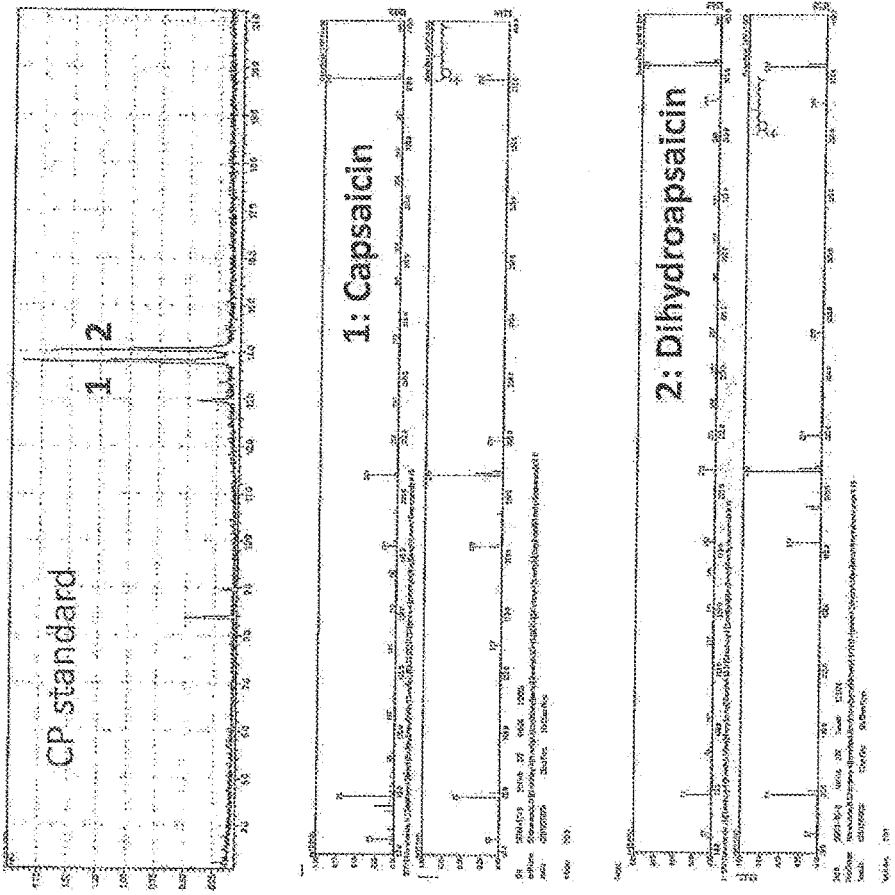
Figure 4:
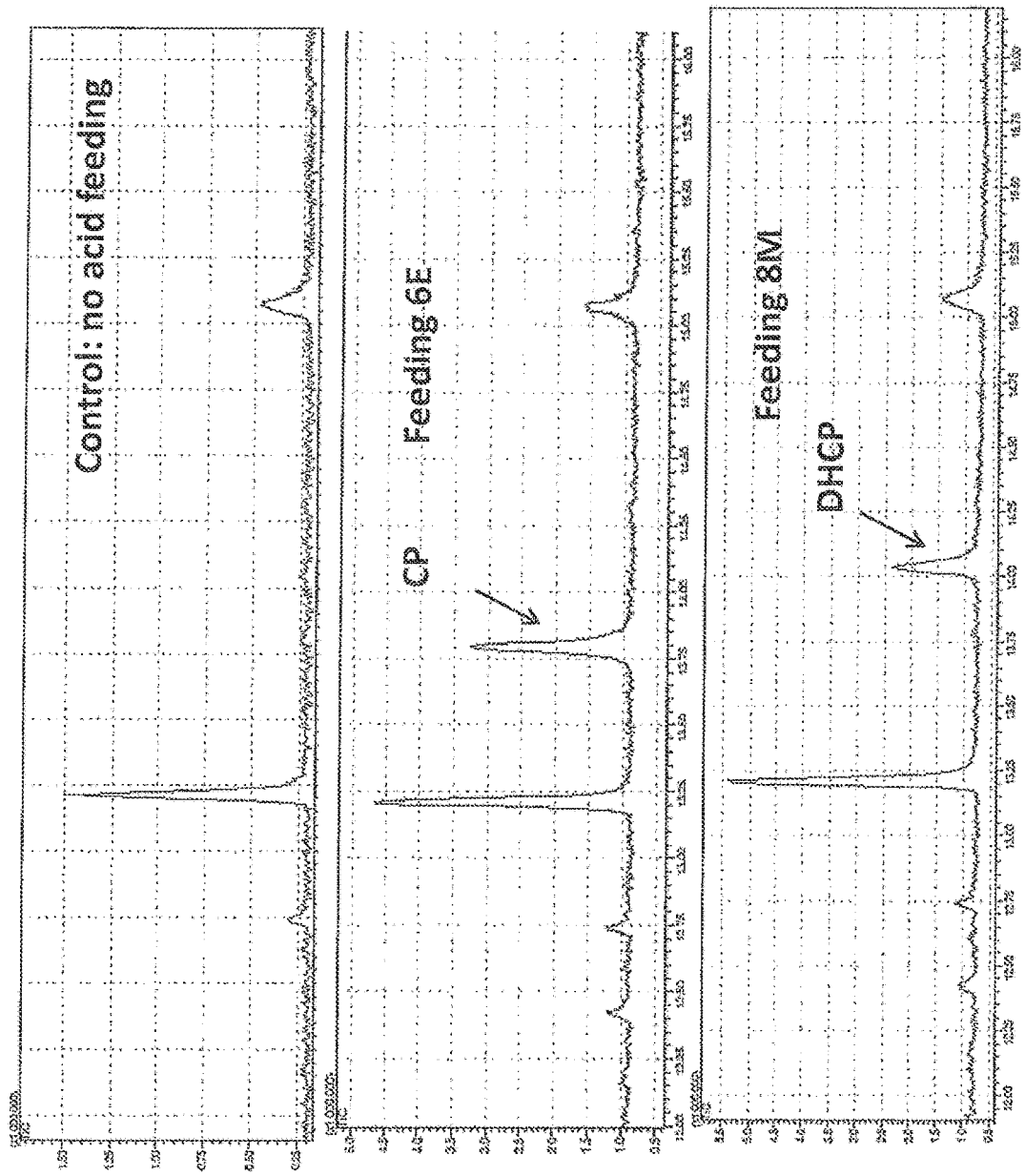
Figure 5:
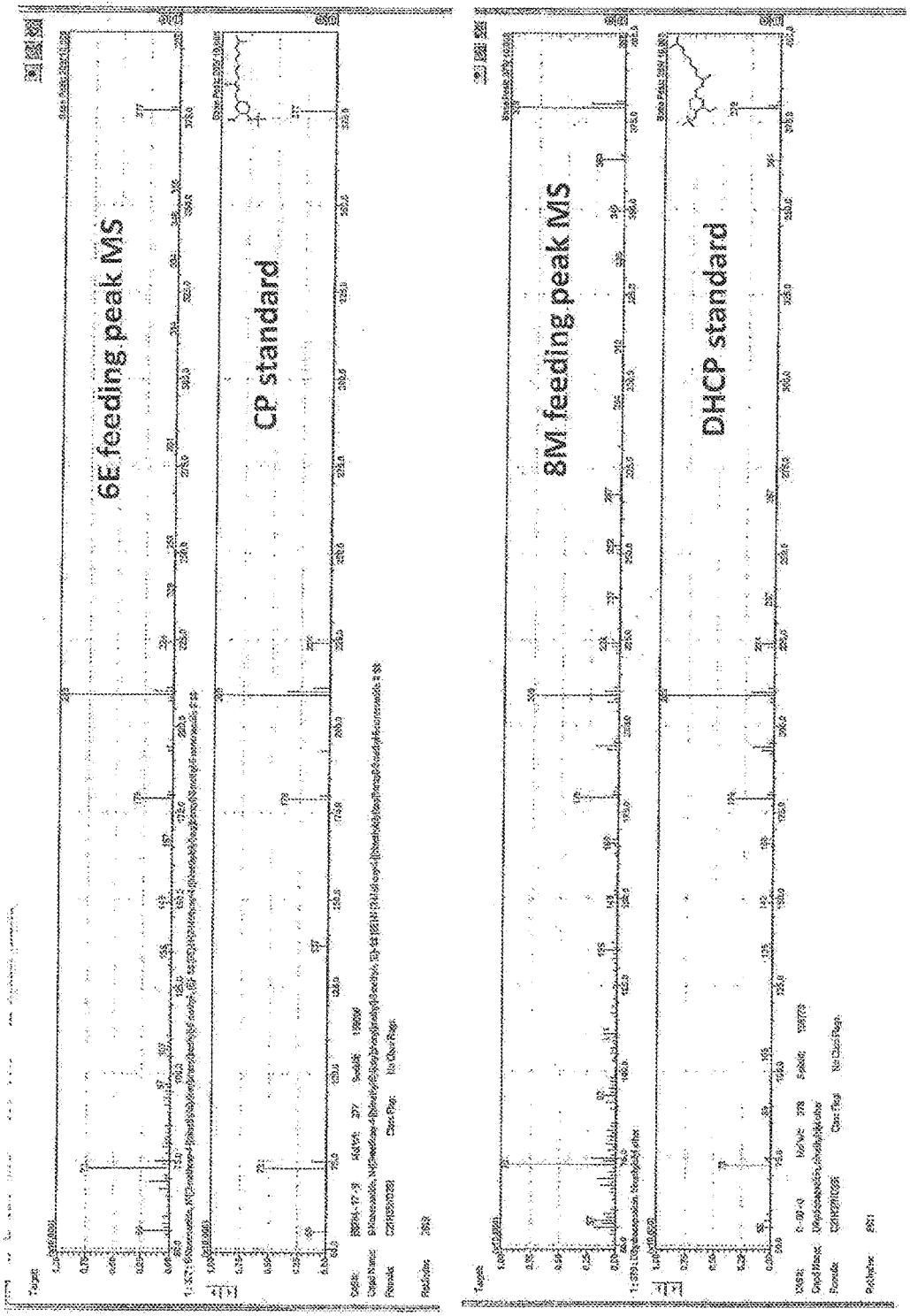

The identity of CP/DHCP was confirmed by further GC/MS analysis. As shown in FIG. 3 (GC/MS profiles), the CP standard from Sigma is actually a mixture of CP and DHCP at a ratio of about 60:40. The retention times are 13.80 and 14.04 min for CP and DHCP, respectively. The MS library in GC/MS machine contains the standard spectra for both CP and DHCP, which match those from the Sigma standard. As shown in FIG. 4, the feeding of 6E and 8M to the culture expressing the gene products of ACS1 and CS/AT3/Pun1 resulted in the production of CP and DHCP, respectively. The spectra of the products match those of the standards very well in a side-by-side comparison (FIG. 5).

CS/Pun1/AT3 Gene Product Has CS Activity In Vitro.

To determine activity in vitro, applicants amplified CS/Pun1/AT3 gene from the cDNA derived from the green fruits of ghost chili pepper using the primers of 309-sumo-F, CGC GAA CAG ATT GGA GGT GCTTTTGCATTAC-CATC and 309-sumo-R, GTG GCG GCC GCT CTA TTA TTAGGCAATGAACTCAAGGAG. The resulting PCR product was purified on 1% agarose gel and combined with linear pETite N-His SUMO Kan expression vector (Lucigen, Middleton, Wis.). The DNA mixture was used to transform HI-control 10G chemically competent cells by heat shock (Lucigen). The gene insertion was then fully sequenced and the sequence was identical to that of Pun1 gene from *Capsicum chinense* (GenBank: AY819027).

Sequence of CS/Pun1/AT3 from ghost chili pepper
SEQ ID No. 1:
ATGGCTTTTGCATTACCATCATCACTTGTTTCAGTTTGTGACAAATCT

TTTATCAAACCTTCCTCTCTCACCCCCTCTAAACTTAGATTTCACAAG

CTATCTTTCATCGATCAATCTTTAAGTAATATGTATATCCCTTGTGCA

TTTTTTTACCCTAAAGTACAACAAAGACTAGAAGACTCCAAAAATTCT

GATGAGCTTTCCCATATAGCCCACTTGCTACAAACATCTCTATCACAA

ACTCTAGTCTCTTACTATCCTTATGCAGGAAAGTTGAAGGACAATGCT

ACTGTTGACTGTAACGATATGGGAGCTGAGTTCTTGAGTGTTCGAATA

AAATGTTCCATGTCTGAAATTCTTGATCATCCTCATGCATCTCTTGCA

GAGAGCATAGTTTTGCCCAAGGATTTGCCTTGGGCGAATAATTGTGAA

GGTGGTAATTTGCTTGTAGTTCAAGTAAGTAAGTTTGATTGTGGGGGA

ATAGCCATCAGTGTATGCTTTTCGCACAAGATTGGTGATGGTTGCTCT

CTGCTTAATTTCCTTAATGATTGGTCTAGCGTTACTCGTGATCATACG

ACAACAGCTTTAGTTCCATCTCCTAGATTTGTAGGAGATTCTGTCTTC

TCTACAAAAAAATATGGTTCTCTTATTACGCCACAAATTTTGTCCGAT

CTCAACGAGTGCGTACAGAAAAGACTCATTTTTCCTACAGATAAGTTA

GATGCACTTCGAGCTAAGGTGGCAGAAGAATCAGGAGTAAAAAATCCA

ACAAGGGCAGAAGTTGTTAGCGCTCTTCTTTTCAAATGTGCAACAAAG

GCATCATCATCAATGCTACCATCAAAGTTGGTTCACTTCTTAAACATA

CGTACTATGATCAAACCTCGTCTACCACGAAATGCCATTGGAAATCTC

TCGTCTATTTTCTCCATAGAAGCAACTAACATGCAGGACATGGAGTTG

CCAACGTTGGTTCGTAATTTAAGGAAGGAAGTTGAGGTGGCATACAAG

AAAGACCAAGTCGAACAAAATGAACTGATCCTAGAAGTAGTAGAATCA

ATGAGAGAAGGGAAACTGCCATTTGAAAATATGGATGGCTATGAGAAT

GTGTATACTTGCAGCAATCTTTGCAAATATCCGTACTACACTGTAGAT

TTTGGATGGGAAGACCTGAAAGAGTGTGTCTAGGAAATGGTCCCTCC

AAGAATGCCTTCTTCTTGAAAGATTACAAAGCTGGGCAAGGCGTGGAG

GCGCGGGTGATGTTGCACAAGCAACAAATGTCTGAATTTGAACGCAAT

GAGGAACTCCTTGAGTTCATTGCCTAA

Figure 6:
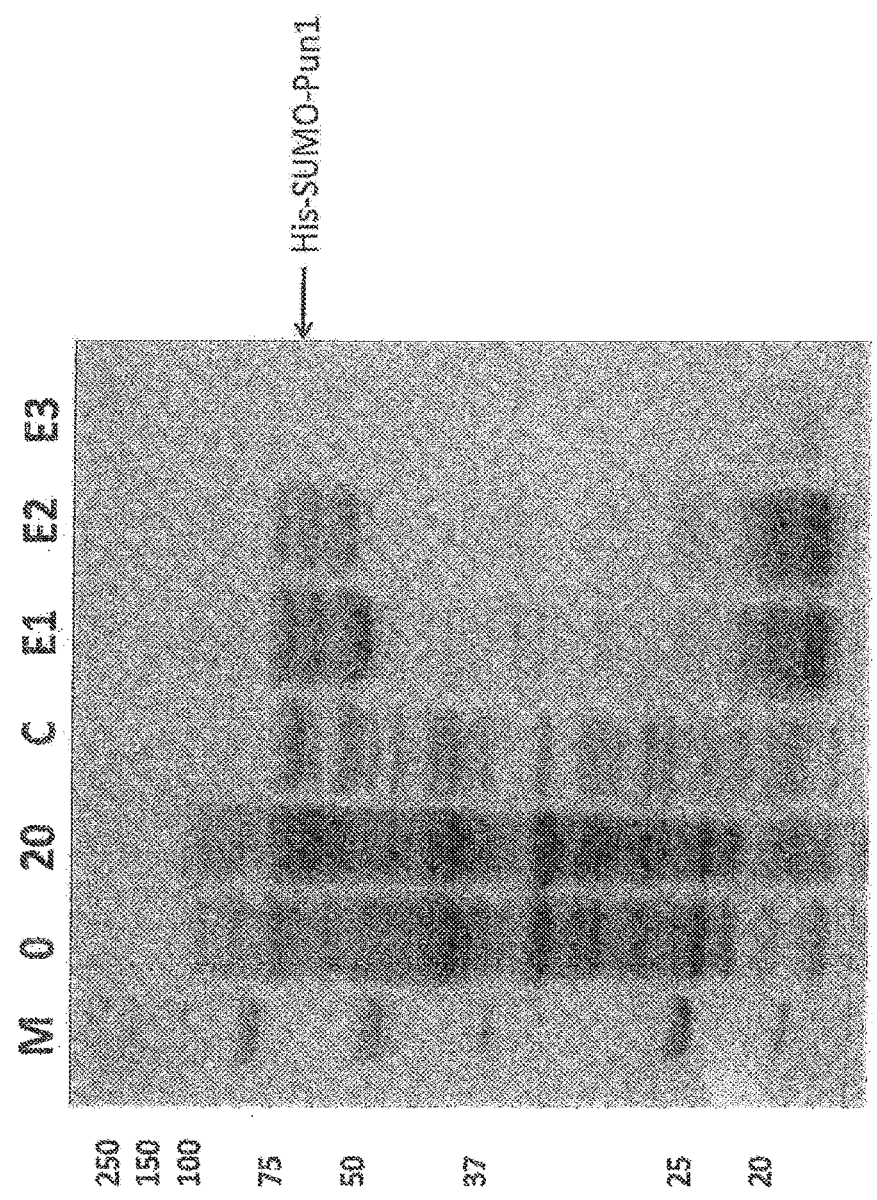

Applicants used pETite N-His SUMO-ghost Pun1 to transform HI-Control BL21(DE3) cells (Lucigen) and the expression of His-SUMO-Pun1 was induced by 0.5 mM IPTG at 16° C. for 20 hrs. The fusion protein was purified by Ni-NTA column (FIG. 6). The gene product of Pun1 has a molecular weight of ca. 49 Kd and the size of His-SUMO tag is ca. 12 Kd. The His-SUMO-CS fusion protein on SDS-PAGE migrated close to the predicted size (ca. 61 Kd) (FIG. 6).

Figure 7:
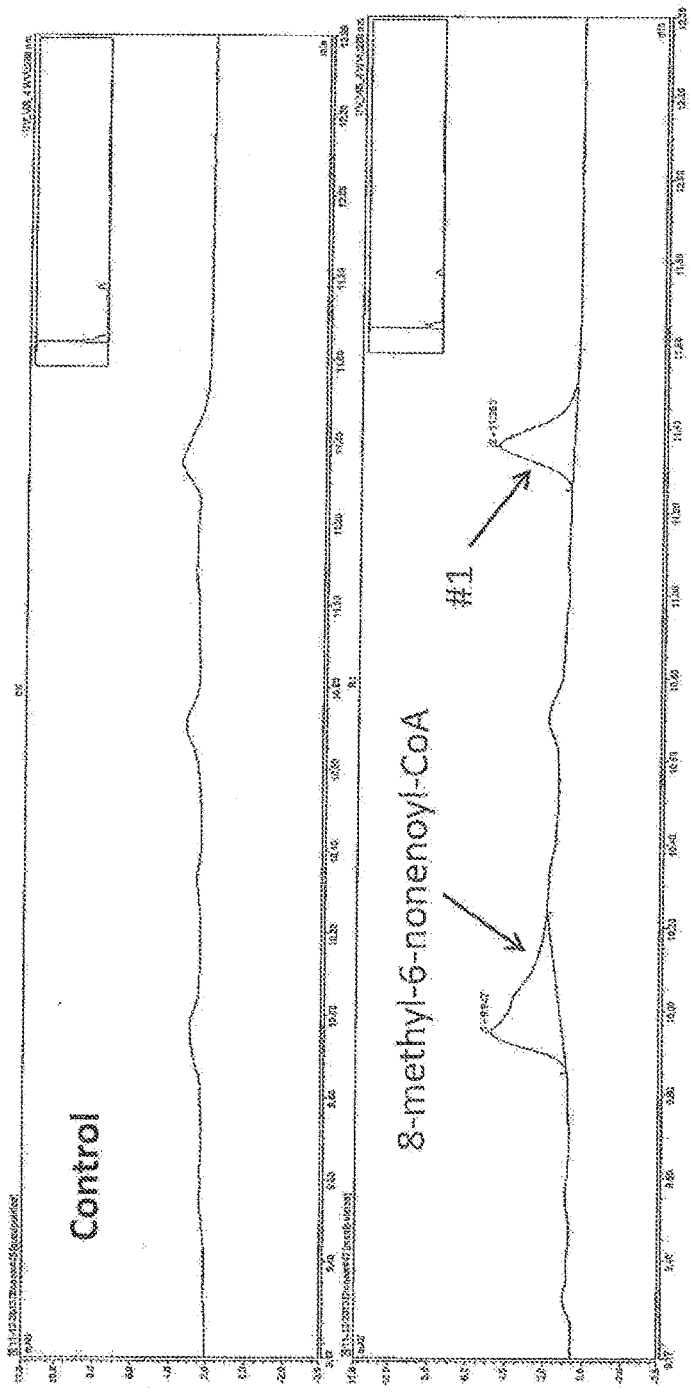
FIG. 7 shows HPLC profile of the products of ACS1 and Pun1 coupled reaction when VN and 6E were used as substrates. #1, putative CP.

Applicants used a ACS1 and CS/Pun1/AT3 coupled enzyme system to assay the activity of the gene product of CS/Pun1/AT3. The gene product of ACS1 facilitates the production of substrates for the gene product of CS/Pun1/AT3. The system includes 100 mM Tris, pH8.5, 5 mM ATP, 0.5 mM CoA, 10 mM $MgCl_2$, 100 mg/L VN, and 1 mM 6E. The rection was started by adding purified SUMO-ACS1 and SUMO-Pun1 simultaneously. The reaction lasted 1 hr before it was terminated by adding acetic acid. The reaction product was first analyzed by HPLC (FIG. 7). Compared to the control, two products were formed one is 8-methyl-6-nonenoyl-CoA, which was previously confirmed by MS/MS (Chen H, Wang H, and Yu O, 2013) and another product (#1) matches the retention time of CP.

Figure 8:
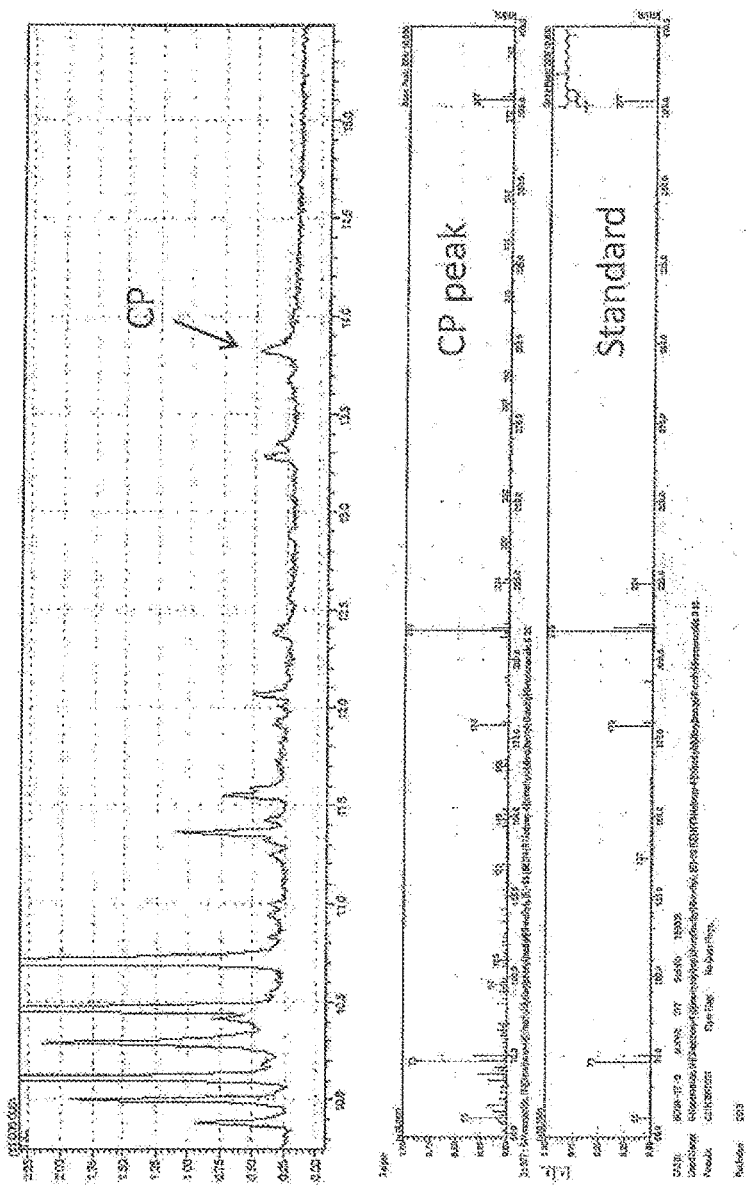
FIG. 8 shows formation of CP (peak #1 in FIG. 7) in vitro by a ACS1-Pun1 coupled enzyme system as analyzed by GC/MS.

To further confirm the identity of peak #1, the ethyl acetate extract was dried over N2 gas and derivatized by MSTFA (N-Methyl-N-(trimethylsilyl) trifluoroacetamide-Sigma). The products were analyzed by GC/MS (FIG. 8). As shown in FIG. 8, the CP produced from the enzymatic reaction has the same MS profile as CP standard.

Figure 9:
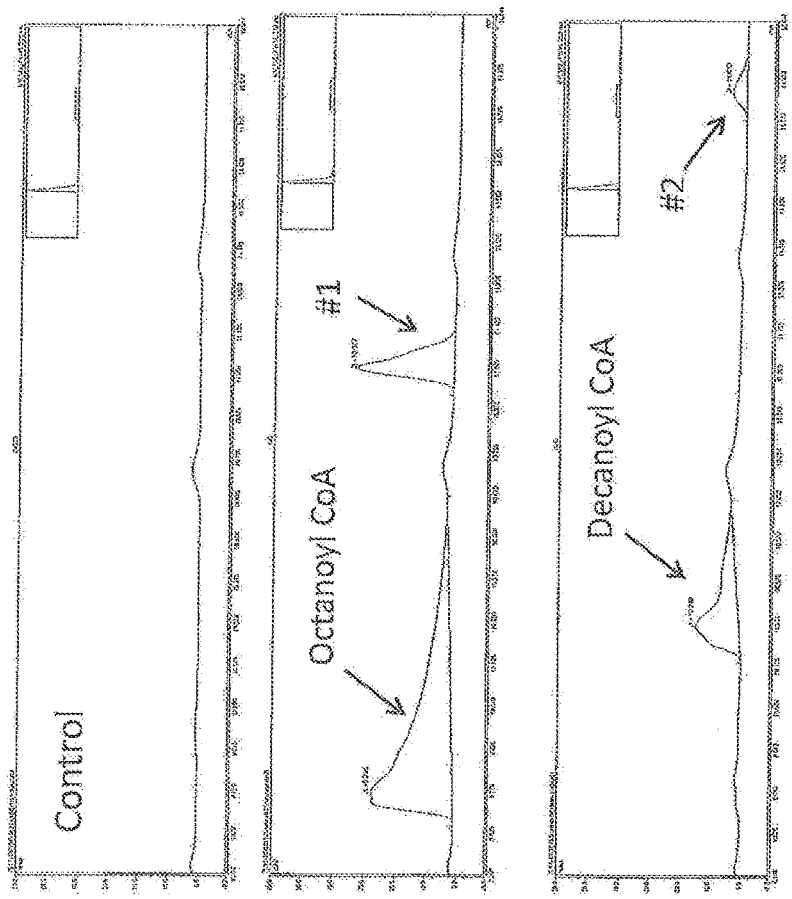
FIG. 9 shows HPLC analysis of Pun1 in vitro activity when octanoyl-CoA or decanoyl-CoA was used as a substrate. #1, putative N-vanillyloctamide; #2, putative N-vanillyldecanamide.
Figure 10:
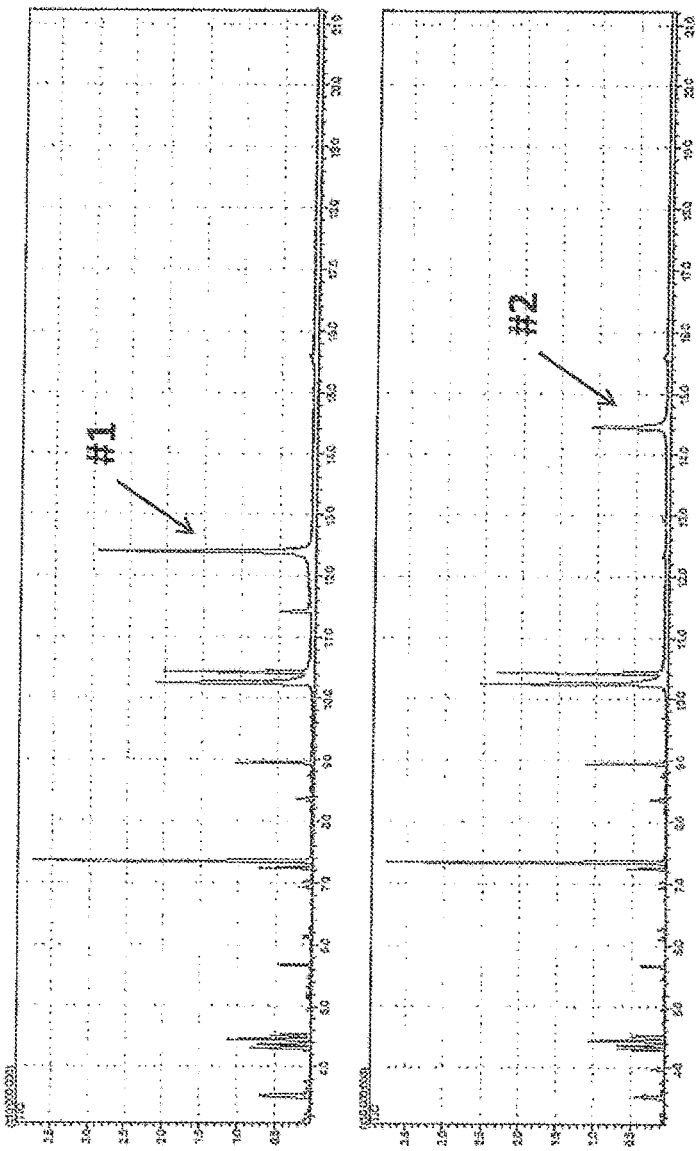
FIG. 10 shows GC/MS analysis of Pun1 in vitro activity when octanoyl-CoA or decanoyl-CoA was used as a substrate. #1, putative N-vanillyloctamide; #2, putative N-vanillyldecanamide.
Figure 11:
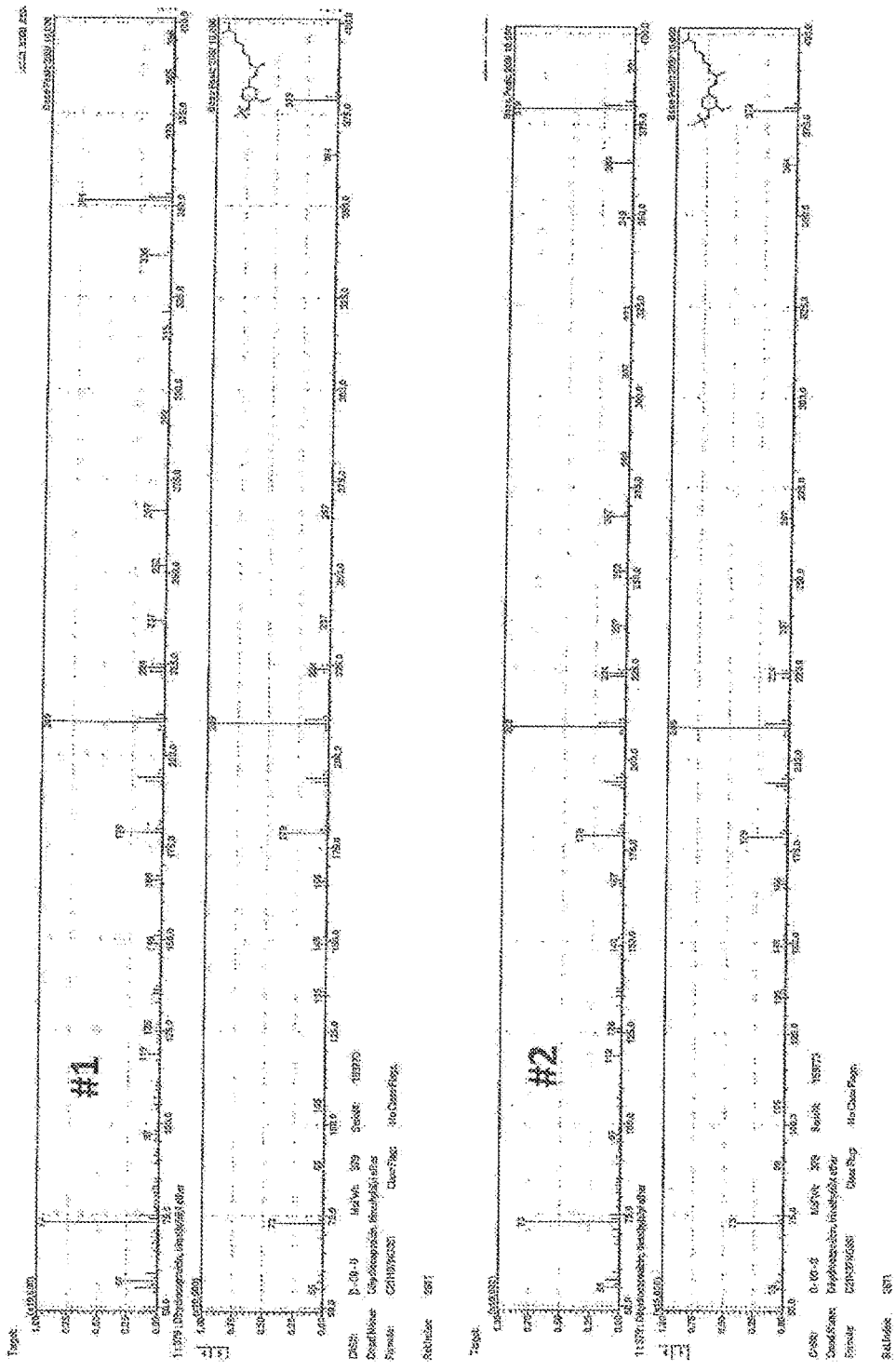
FIG. 11 shows the MS profiles of peaks #1 and #2 of FIG. 10. #1, N-vanillyloctamide; #2, N-vanillyldecanamide.

In addition, applicants also tested the activity using other substrates. Applicants purchased octanoyl CoA and decanoyl CoA from Sigma. When these acyl-CoAs and VN were used together as substrates, the corresponding capsaicinoids (#1 and #2 for N-vanillyloctamide and N-vanillyldecanamide, respectively) were formed, confirming the enzymatic activity of Pun1 (FIGS. 9 and 10). The enzyme products were extracted with ethyl acetate and dried over $N_2$ gas. The MSTFA derivatives were analyzed by GC/MS. FIG. 11 shows the MS profiles of peaks #1 and #2 of FIG. 10.

EXAMPLE 2

Cloning

ACS1 gene was PCR amplified from pETite N-His SUMO-ghost ACS1 template using the primers of ACS1-Bgl ll-F: GAAGATCTATGGCAACAGATAAATTTA and ACS1-XhoI-R: CCGCTCGAGTCACTTGGTACCCTTG-TAC and ligated into the MCS2 site of pCDFDuet-1 vector (Novagen). The resulting plasmid pCDFDuet-ACS1 was used to transform competent *E. coli* BL21(DE3) cells. The transformed cells were selected on LB plate containing 100 mg/L of spectinomycin. The resulting BL21(DE3) cells harboring pCDFDuet-ACS1 was used for the second transformation with pETite N-His SUMO-ghost Pun1 vector. The transformants were selected on LB plates containing 50 mg/L of kanamycin and 100 mg/L of spectinomycin.

Different Culture Media

Different culture media were tested for CP (capsaicin) production in the BL21(DE3) culture co-overexpressing ACS1 and Pun1 upon the feeding of VN (vanillyamine) and 6E (8-methyl-6-nonenoic acid). Briefly, an overnight culture was used to inoculate liquid LB, TB or M9 medium (2%) containing 50 mg/L of kanamycin and 100 mg/L of spectinomycin. The culture was first grown at 37° C. to an OD600 of 0.6 and cooled down to 16° C. Then 1 mM IPTG was added to induce the expression of ACS1 and Pun1. After 1 h of incubation at 16° C., 50 mg/L of VN and 50 mg/L of 6E were added to the culture and the culture was continued to be incubated at 16° C. Samples were taken at 0, 18, 22, 26, 42 and 48 h after the feeding of substrates. CP was extracted by ethyl acetate and analyzed by HPLC. FIG. 12 shows that among the three media tested, TB was the best for CP production from VN and 6E.

Identity and Similarity

Identity is the fraction of amino acids that are the same between a pair of sequences after an alignment of the sequences (which can be done using only sequence information or structural information or some other information, but usually it is based on sequence information alone), and similarity is the score assigned based on an alignment using some similarity matrix. The similarity index can be any one of the following BLOSUM62, PAM250, or GONNET, or any matrix used by one skilled in the art for the sequence alignment of proteins.

Identity is the degree of correspondence between two sub-sequences (no gaps between the sequences). An identity of 25% or higher implies similarity of function, while 18-25% implies similarity of structure or function. Keep in mind that two completely unrelated or random sequences (that are greater than 100 residues) can have higher than 20% identity. Similarity is the degree of resemblance between two sequences when they are compared. This is dependent on their identity.

As is evident from the foregoing description, certain aspects of the present disclosure are not limited by the particular details of the examples illustrated herein, and it is therefore contemplated that other modifications and applications, or equivalents thereof, will occur to those skilled in the art. It is accordingly intended that the claims shall cover all such modifications and applications that do not depart from the spirit and scope of the present disclosure.

Moreover, unless defined otherwise, all technical and scientific terms used herein have the same meaning as commonly understood by one of ordinary skill in the art to which the disclosure belongs. Although any methods and materials similar to or equivalent to or those described herein can be used in the practice or testing of the present disclosure, the preferred methods and materials are described above.

Other aspects, objects and advantages of the present disclosure can be obtained from a study of the drawings, the disclosure and the appended claims.

REFERENCES

Aza-González C, Núñez-Palenius H G, Ochoa-Alejo N. (2011) Molecular biology of capsaicinoid biosynthesis in chili pepper (*Capsicum* spp.). Plant Cell Rep. 30: 695-706.

Chen H, Wang H, and Yu O (2013) METHOD OF USING ACYL-COA SYNTHETASE FOR BIOSYNTHETIC PRODUCTION OF ACYL-COA. U.S. Provisional Patent Application No. 61/898,944, filed on Nov. 1, 2013

Curry J, Aluru M, Mendoza M, Nevarez J, Melendrez M, O'Connell M A. (1999) Transcripts for possible capsaicinoid biosynthetic genes are differentially accumulated in pungent and non-pungent *Capsicum* spp. Plant Sci 148: 47-57.

Du J, Shao Z, Zhao H. (2011) Engineering microbial factories for synthesis of value-added products. J Ind Microbiol Biotechnol. 38: 873-890.

Garcés-Claver A, Gil-Ortega R, Alvarez-Fernández A, Arnedo-Andres M S. (2007) Inheritance of capsaicin and dihydrocapsaicin, determined by HPLC-ESI/MS, in an intraspecific cross of *Capsicum annuum* L. J Agric Food Chem. 55: 6951-6957.

Häusler A, and Münch T. (1997) Microbial production of natural flavors. ASM News 63:551-559.

Kim J S, Park M, Lee D J, Kim B D. (2009) Characterization of putative capsaicin synthase promoter activity. Mol Cells. 28: 331-339.

Liang Y T, Tian X Y, Chen J N, Peng C, Ma K Y, Zuo V, Jiao R, Lu Y, Huang Y, Chen Z Y. (2013) Capsaicinoids lower plasma cholesterol and improve endothelial function in hamsters. Eur J Nutr. 52: 379-388.

Mazourek M, Pujar A, Borovsky Y, Paran I, Mueller L, Jahn M M. (2009) A dynamic interface for capsaicinoid systems biology. Plant Physiol. 150: 1806-1821.

Prasad B C, Kumar V, Gururaj H B, Parimalan R, Giridhar P, Ravishankar G A. (2006) Characterization of capsaicin synthase and identification of its gene (csy1) for pungency factor capsaicin in pepper (*Capsicum* sp.). Proc Natl Acad Sci USA. 103: 13315-13320.

Prasad B C, Kumar V, Gururaj H B, Parimalan R, Giridhar P, Ravishankar G A. (2008) Retraction for Prasad et al., Characterization of capsaicin synthase and identification of its gene (csyl) for pungency factor capsaicin in pepper (*Capsicum* sp.). Proc Nat) Acad Sci USA. 105: 20558.

Reilly C A, Crouc D J, Yost G S, Fatah A A. (2001) Determination of capsaicin, dihydrocapsaicin, and nonivamide in self-defense weapons by liquid chromatography-mass spectrometry and liquid chromatography-tandem mass spectrometry. J Chromatogr A. 912: 259-267.

Stewart C Jr, Kang B C, Liu K, Mazourek M, Moore S L, Yoo E Y, Kim B D, Paran I, Jahn M M. (2005) The Pun1 gene for pungency in pepper encodes a putative acyltransferase. Plant J. 42: 675-688.

Stewart C Jr, Mazourek M, Stellari G M, O'Connell M, Jahn M. (2007) Genetic control of pungency in *C. chinense* via the Pun1 locus. J Exp Bot. 58: 979-991.

Thomas B V, Schreiber A A, and Weisskopf C P (1998) Simple method for quantitation of capsaicinoids in peppers using capillary gas chromatography. J Agric Food Chem 46:2655-2663.

Webber H. (1911) Preliminary notes on pepper hybrids. Am. Breed. Assoc. Annu. Rep. 7, 188-199.

The claims are the following:

1. A bioconversion method of making a capsaicinoid comprising:
   (a) expressing a first gene product of CS/AT3/Pun1 in a mixture;
   (b) providing a first substrate to the mixture;
   (c) expressing a second gene product of ACS1 in said mixture;
   (d) providing a second substrate to the mixture;
   (e) collecting the capsaicinoid; and,
   wherein the CS/AT3/Pun1 comprises the DNA sequence of SEQ ID No. 1 wherein the gene products are first expressed within a cellular system.

2. The bioconversion method of making a capsaicinoid of claim 1, wherein the CS/AT3/Pun1 DNA sequence is derived from ghost chili pepper.

3. The bioconversion method of making a capsaicinoid of claim 1, wherein the first substrate is an activated fatty acid selected from the group consisting of 8-methyl-6-nonenoyl-CoA, 8-methyl nonanoyl-CoA, octanoyl-CoA, decanoyl-CoA, other medium to long-chain acyl CoAs and a combination thereof.

4. The bioconversion method of making a capsaicinoid of claim 1, wherein the ACS1 is derived from ghost chili pepper.

5. The bioconversion method of making a capsaicinoid of claim 1, wherein the second substrate is a fatty acid selected from the group consisting of 8-methyl-6-nonenoic acid, 8-methyl nonanoic acid, octanoic acid, decanoic acid, other medium-to long-chain fatty acids and a combination thereof.

6. The bioconversion method of making a capsaicinoid acid of claim 1, wherein the cellular system comprises a microorganism selected from the group consisting of bacteria, yeast and a combination thereof.

7. The bioconversion method of making a capsaicinoid of claim 1, further comprising providing a third substrate vanillylamine.

8. The bioconversion method of making a capsaicinoid acid of claim 7, wherein the cellular system comprises a microorganism selected from the group consisting of bacteria, yeast and a combination thereof.

9. A bioconversion method of making a capsaicinoid comprising:
   (a) expressing a gene product of CS/AT3/Pun1 in a cellular system;
   (b) providing fatty acid-CoA;
   (c) expressing a second gene product of ACS1 in said cellular system;
   (d) providing vanillylamine;
   (e) growing the cellular system in a medium;
   (f) collecting the capsaicinoid; and,
   wherein the of CS/AT3/Pun1 comprises the DNA sequence of SEQ ID No. 1 and wherein the gene products are expressed within said cellular system.

10. The bioconversion method of making a capsaicinoid acid of claim 9, wherein the cellular system comprises a microorganism selected from the group consisting of bacteria, yeast and a combination thereof.

* * * * *

UNITED STATES PATENT AND TRADEMARK OFFICE
CERTIFICATE OF CORRECTION

PATENT NO. : 9,951,358 B2
APPLICATION NO. : 15/111901
DATED : April 24, 2018
INVENTOR(S) : Hui Chen et al.

It is certified that error appears in the above-identified patent and that said Letters Patent is hereby corrected as shown below:

In the Claims

In Claim 9, Column 16, Line 23:
"wherein the of CS/AT3/Pun1 comprises the DNA" should be replaced with the text -- wherein the CS/AT3/Pun1 comprises the DNA --

Signed and Sealed this
Twenty-fourth Day of July, 2018

Andrei Iancu
*Director of the United States Patent and Trademark Office*